US009171444B2

(12) United States Patent
Koblasz

(10) Patent No.: US 9,171,444 B2
(45) Date of Patent: *Oct. 27, 2015

(54) HEALTHCARE WORKSTATIONS AND RFID DEVICES FOR DETECTING MEDICATION ERRORS, FALLS AND WANDERING

(71) Applicant: GT Angel, LLC, Atlanta, GA (US)

(72) Inventor: Arthur Koblasz, Atlanta, GA (US)

(73) Assignee: GT Angel, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,025

(22) Filed: Nov. 4, 2014

(65) Prior Publication Data
US 2015/0048949 A1 Feb. 19, 2015

Related U.S. Application Data

(63) Continuation of application No. 11/804,068, filed on May 16, 2007, now Pat. No. 8,878,676.

(51) Int. Cl.
G08B 21/22 (2006.01)
G01S 1/02 (2010.01)
G01S 5/02 (2010.01)
G01S 5/04 (2006.01)
G08B 21/02 (2006.01)
G06F 19/00 (2011.01)

(52) U.S. Cl.
CPC ........ *G08B 21/0261* (2013.01); *G06F 19/3462* (2013.01); *G06F 19/323* (2013.01)

(58) Field of Classification Search
None
See application file for complete search history.

(56) References Cited

U.S. PATENT DOCUMENTS

| 3,921,621 | A | * | 11/1975 | Baessler | 600/549 |
| 4,907,845 | A | * | 3/1990 | Wood | 340/573.4 |
| 4,991,585 | A | * | 2/1991 | Mawhinney | 600/430 |
| 5,107,855 | A | * | 4/1992 | Harrington et al. | 600/534 |
| 5,405,011 | A | * | 4/1995 | Haber et al. | 206/531 |
| 5,405,048 | A | * | 4/1995 | Rogers et al. | 221/211 |
| 5,564,803 | A | * | 10/1996 | McDonald et al. | 312/215 |
| 5,575,392 | A | * | 11/1996 | Cutler | 206/534 |
| 5,609,268 | A | * | 3/1997 | Shaw | 221/2 |
| 5,641,091 | A | * | 6/1997 | Daneshvar | 221/3 |
| 5,700,998 | A | * | 12/1997 | Palti | 235/375 |
| 5,883,806 | A | * | 3/1999 | Meador et al. | 700/244 |
| 5,963,136 | A | * | 10/1999 | O'Brien | 340/573.1 |
| 6,189,727 | B1 | * | 2/2001 | Shoenfeld | 221/2 |

(Continued)

Primary Examiner — Brian Zimmerman
Assistant Examiner — Cal Eustaquio
(74) Attorney, Agent, or Firm — Minh N. Nguyen; Next IP Law Group LLP

(57) ABSTRACT

A medication administration system that includes a system of pillboxes, a pharmacy workstation, and a system of attendant workstation. The pharmacy workstation reads RFID or barcode tags on the pillboxes and medication wrappers containing medication units as the medication units are checked into the pillboxes to ensure that the pillboxes are filled in accordance the appropriate prescription regimens. The attendant workstations read the RFID or barcode tags on the pillboxes and medication wrappers as the medication units are checked out of the pillboxes to ensure that the medications are administered in accordance the appropriate prescription regimens. The attendant workstations may activate alarms, which may include communicating the alarms to a central monitoring station or mobile communication devices assigned to healthcare providers, when the determine that a pillbox in not correctly filled, when a medication has been checked out of a pillbox improperly, or when a medication has not been checked out on time.

22 Claims, 6 Drawing Sheets

(56) References Cited

U.S. PATENT DOCUMENTS

| | | | |
|---|---|---|---|
| 6,380,858 B1* | 4/2002 | Yarin et al. | 340/573.1 |
| 6,851,615 B2* | 2/2005 | Jones | 235/487 |
| 6,961,285 B2* | 11/2005 | Niemiec et al. | 368/10 |
| 6,975,922 B2* | 12/2005 | Duncan et al. | 700/242 |
| 7,035,168 B2* | 4/2006 | Niemiec et al. | 368/10 |
| 7,080,755 B2* | 7/2006 | Handfield et al. | 221/13 |
| 7,091,864 B2* | 8/2006 | Veitch et al. | 340/572.8 |
| 7,132,940 B2* | 11/2006 | Ehben et al. | 340/539.21 |
| 7,146,247 B2* | 12/2006 | Kirsch et al. | 700/236 |
| 7,154,397 B2* | 12/2006 | Zerhusen et al. | 340/573.1 |
| 7,156,305 B2* | 1/2007 | Swan et al. | 235/385 |
| 7,158,030 B2* | 1/2007 | Chung | 340/572.1 |
| 7,175,081 B2* | 2/2007 | Andreasson et al. | 235/385 |
| 7,177,721 B2* | 2/2007 | Kirsch et al. | 700/236 |
| 7,178,729 B2* | 2/2007 | Shaffer et al. | 235/385 |
| 7,203,571 B2* | 4/2007 | Kirsch et al. | 700/236 |
| 2001/0009042 A1* | 7/2001 | Ruschke | 5/600 |
| 2002/0027507 A1* | 3/2002 | Yarin et al. | 340/573.1 |
| 2002/0047075 A1* | 4/2002 | Metz et al. | 248/229.1 |
| 2002/0060630 A1* | 5/2002 | Power | 340/573.1 |
| 2002/0145526 A1* | 10/2002 | Friedman et al. | 340/573.5 |
| 2002/0185532 A1* | 12/2002 | Berquist et al. | 235/385 |
| 2003/0006878 A1* | 1/2003 | Chung | 340/5.25 |
| 2003/0146839 A1* | 8/2003 | Ehlers et al. | 340/572.7 |
| 2003/0164401 A1* | 9/2003 | Andreasson et al. | 235/385 |
| 2003/0229518 A1* | 12/2003 | Abraham-Fuchs et al. | 705/2 |
| 2004/0183683 A1* | 9/2004 | Funahashi | 340/573.1 |
| 2004/0225199 A1* | 11/2004 | Evanyk et al. | 600/300 |
| 2006/0058917 A1* | 3/2006 | Vonk et al. | 700/236 |
| 2006/0119481 A1* | 6/2006 | Tethrake et al. | 340/572.1 |
| 2006/0148423 A1* | 7/2006 | Sharpe | 455/90.1 |
| 2007/0203755 A1* | 8/2007 | Willson et al. | 705/3 |
| 2009/0256750 A1* | 10/2009 | Mathews et al. | 342/450 |

* cited by examiner

HEALTHCARE WORKSTATIONS AND RFID DEVICES FOR DETECTING MEDICATION ERRORS, FALLS AND WANDERING

CROSS REFERENCE TO RELATED APPLICATIONS

This application is a continuation of copending U.S. utility application entitled, "Healthcare Workstations and RFID Devices for Detecting Medication Errors," having Ser. No. 11/804,068, filed on May 16, 2007, which claims the benefit of U.S. provisional application entitled, "Computer Aided Nursing Devices and Methods," having Ser. No. 60/800,658, filed on May 16, 2006, all of which are entirely incorporated herein by reference.

TECHNICAL FIELD

This application relates to healthcare workstations for use by nurses and other healthcare providers in hospitals and other healthcare facilities and, more particularly, to a healthcare workstation with an RFID monitoring and alarm system.

BACKGROUND OF THE INVENTION

In a study of more than 1000 hospitals in the U.S. reported in the Pharmacotherapy Journal in 2001, medication errors occurred in 5.07% of the patients admitted and 0.25% of the patients were seriously injured. On the average, each hospital committed one medication error every 22.7 hours. According to a report published by the American Institute of Medicine in 2006, the total cost for medication errors is more than $3.5 Billion/year, but this estimate does not include the cost for extended care. In a study of 36 hospitals and nursing homes in Colorado and Georgia reported in the Archives of Internal Medicine in September 2003, the most common drug error is giving hospitalized patients their medications at the wrong times or not at all. In 2001, the American Association of Critical-Care Nurses reported that distractions cause 36% of the reported medication errors in the U.S.

Many patents have been issued for devices that automatically dispense pills, such as U.S. Pat. No. 5,405,011 issued to Haber, et al. in April 1995, U.S. Pat. No. 5,575,392 issued to Cutler in November 1996, U.S. Pat. No. 5,641,091 issued to Daneshvar in June 1997, and U.S. Pat. No. 5,609,268 issued to Shaw in March 1997. None of these inventions use RFID tags or barcode labels to identify the medication or the patient.

U.S. Pat. No. 5,700,998 issued to Palti in December 1997, describes a simple concept of printing a linear or radial barcode label directly onto each pill. In another noteworthy invention, U.S. Pat. No. 5,564,803 issued to McDonald, et al. in October 1996 describes a "portable nursing center" attached to a cart with wheels. The data entry is via a keypad, barcode reader or touch screen; therefore, both the patient and the medications can be identified via barcode labels. The cart contains drawers that automatically open to access pills for an identified patient, and the cart computer also provides access to patient records. Some hospitals like this method for delivering medications, but it assigns most of the delivery workload to nurses, and the nurses are already overworked and understaffed. Furthermore, infectious organisms can be easily carried from room to room via the cart.

Some hospitals believe it is more cost effective to store medications inside stationary locked cabinets at central locations, such as one cabinet on each nurses' station, floor or wing of a hospital. U.S. Pat. No. 5,405,048 issued to Rogers, et al. in April 1995 describes a medication storage cabinet with separate compartments for pills and a vacuum operated mechanism for individually dispensing pills into a cup. U.S. Pat. No. 5,883,806 issued to Meador, et al. in March 1999 describes a large drug dispensing cabinet with drawers that automatically open when a request is input via a keyboard. U.S. Pat. No. 6,975,922 issued to Duncan, et al. in May 2003 describes an instrumented cabinet with bins and a variety of drawers which contain supplies that could include medications. The configuration of the cabinet proposed by Duncan, et al. is not appropriate for a hallway in a large hospital, but it would be appropriate for a supply cabinet at a nurses' station. A computer guides the worker in finding each requested item by turning on a light at the location in the cabinet where the item is stored. The light does not blink to indicate the number of medications needed for a pillbox.

Most prescribed medications in hospitals are administered at standard times; therefore, the line at a central medication cabinet can get very long just before the standard medication times each day and evening. More important, this delivery scheme requires each nurse to collect all of the medications for several patients at the same time, which could add up to more than 50 medications. Missing pills and other medication errors are more likely to occur in this delivery scheme, but pharmacy workers like the idea of refilling a small number of locked cabinets in the hospital each day. It is important to remember that nurses are making the vast majority of the medication errors occurring in hospitals and nursing homes, and they need help.

A point-of-care computer system is described in U.S. Pat. No. 7,154,397 issued to Zerhan, et al. in December 2006. The point-of-care computer and other electronics are contained inside a bedside frame. The computer controls bed motors, provides access to patient records, and receives data from diagnostic, treatment, and therapy devices. The point-of-care computer also interfaces with a barcode, RFID or other readers for identifying the patient, attendants and medications. When a caregiver brings a "locked medical box" to the patient's room, the patient and medications are scanned by the attendant to verify that the medications match the pharmacy records for the patient. The locked medical box can be attached to different described carts.

Most nurses like the concept of a medication workstation close to each patient room, but there are several problems with the Zerhan invention. If medications and medical supplies are kept inside the patient room, infectious organisms could be easily passed on to the next patient via the storage cabinet. Also, pharmacy workers would not like the idea of delivering a "locked medical box" to a workstation inside each patient room. The rooms could be congested or inaccessible, and any medical boxes left in the hallway could be stolen. If nurses deliver each medical box via a cart or other means, they would be reverting to the delivery methods described in the McDonald patent of 1996, except there would be a separate locked medical box for each patient. The additional workload for nurses would be unacceptable to nursing supervisors.

Several of the above inventions mention RFID tags as an alternative to barcode labels and RFID is an important part of my invention. Passive RFID tags can be used to identify medication containers, supplies, equipment, patients and staff in hospitals. The recent shift from barcode to passive RFID is mostly driven by the fact that RFID transceivers operating at 13.56 MHz and higher frequencies are able to read a large number of tags at the same time, plus the additional advantage that a high-power RFID antenna can be located several feet away from an identified passive tag. If the RFID tag is active (i.e. powered by a battery), the distance between the antenna and the identified tag can be more than 10 feet. It is important to realize that any RFID tag can be easily shielded by wrapping aluminum foil around the tag; therefore RFID tags will never replace barcode readers at the checkout counter in Wal-Mart® stores. For the same reason, it is unlikely that RFID tags will be 100% effective in preventing theft of equipment, medications or babies in hospitals.

Another important limitation of RFID is related to the frequencies of the RF signals transmitted and received by RFID antennas. Higher frequency RFID systems can read a large number of tags at the same time via frequency hopping and other schemes. But at higher frequencies, the smaller wavelengths are not able to go through or around large conductive objects. For example, metal shelves, carts and human bodies can easily block passive RFID readers designed to operate at 2.4 GHz; therefore line of sight communications may be required between a high-frequency RFID antenna and matching tags. RFID signals at 134 KHz are better able to pass around human bodies, but 134 KHz readers are easily jammed by multiple tags.

At some time in the near future, the pharmaceutical industry will hopefully offer wrapped pills with RFID tags instead of barcode labels. More information can be written on an RFID tag, including secret codes that identify the pharmaceutical companies. The latter feature will help prevent counterfeit drugs. U.S. Pat. No. 7,156,305 issued to Swan, et al. in Jan 2007 presents several novel concepts related to RFID tags on medication containers, e.g. identifying counterfeit drugs, improper return of a medication, and supply chain abuses.

U.S. Pat. No. 7,091,864 issued to Veitch, et al. in August 2006 describes a research application of attaching a large number of RFID tags to containers in pharmaceutical studies. In this application, details about each specimen are written on the RFID tag. This invention is not a system for monitoring patients, pillboxes or equipment in healthcare facilities, and hospitals would not like the concept of fabricating custom RFID tags for each patient.

U.S. Pat. No. 7,175,081 issued to Andreasson, et al. in February 2007 describes how a large number of medications with an RFID tag on each medication can be quickly identified using an RFID reader inside a locked "medication-dispensing unit" to determine which medications have been removed from the cabinet and when one of the medications needs to be replenished. Access to the locked cabinet requires the healthcare worker to be identified via an electronic card, PIN or RFID tag. It is then possible to identify if the worker has removed the correct medications for an identified patient or when a pharmacy worker has placed an incorrect medication in one of the compartments inside the cabinet.

Unfortunately, there is a limit to the number of passive RFID tags that can be read at the same time. The current state of the art limits the number of passive RFID tags to a number much smaller than the typical number of medications stored in a medication-dispensing unit on each floor of a hospital. The above inventors solved this problem by providing a separate RFID antenna for each compartment inside the cabinet. This approach requires a large number of RFID antennas and associated equipment.

SUMMARY OF THE INVENTION

The present invention meets the needs described above in a medication administration system that includes a system of pillboxes, a pharmacy workstation, and a system of attendant workstation. The pharmacy workstation reads RFID or barcode tags on the pillboxes and medication wrappers containing medication units as the medication units are checked into the pillboxes to ensure that the pillboxes are filled in accordance the appropriate prescription regimens. The attendant workstations read the RFID or barcode tags on the pillboxes and medication wrappers as the medication units are checked out of the pillboxes to ensure that the medications are administered in accordance the appropriate prescription regimens. The attendant workstations may activate alarms, which may include communicating the alarms to a central monitoring station or mobile communication devices assigned to healthcare providers, when the determine that a pillbox in not correctly filled, when a medication has been checked out of a pillbox improperly, or when a medication has not been checked out on time.

The medication administration system may also assign two pillboxes to each patient, and providing an attendant workstation inside or close to the patient's room. One of the two pillboxes assigned to each patient will contain the patient's medications for the current day and will be stored in a locked compartment of the attendant workstation. The other pillbox will be located in the pharmacy department or at the nurses' station, where it will be filled with the patient's medications for the next day.

The pharmacy workstation is typically located in the pharmacy department or selected nurses' station where the pillboxes are filled. The attendant workstations may also monitor a variety of RF antennas inside the patient's room and at other locations. Each attendant workstation can be mounted to a wall at a convenient location just outside the patient's room. This location reduces the likelihood of passing infectious organisms to the next patient, makes the pharmacy deliveries easier, and gives the attendants more privacy while reviewing and typing patient records. In nursing homes and assistive living centers, the patients are assigned to their rooms for longer periods, and the medications are handled differently. These institutions may prefer to mount each attendant workstation to a computer desk or to the patient's bed frame. In the bed frame version of the attendant workstation, the workstation cabinet can be modified to plug into existing slots for a trapeze frame, and the workstation can include a second monitor and wireless keyboard for the patient. A camera, microphone and speaker may also be attached to the workstation cabinet for video communications with the patient.

In hospitals, each medication will be individually wrapped with a barcode or RFID tag attached to each medication wrapper. Each medication tag will identify the quantity and type of the medication. Each pillbox will be also identified by a barcode or RFID tag attached to the pillbox indicating an ID code previously assigned to the patient. The second pillbox assigned to each patient will be identified by the same or different ID code. The attendant workstation will contain a barcode reader plus one or more RFID readers for identifying each pillbox tag and for identifying each medication wrapper tag. If an RFID tag is attached to each medication wrapper, all of the medications inside the pillbox will be scanned at the same time by an RFID reader inside the attendant workstation to detect when an arriving pillbox contains incorrect or missing medications or when a nurse has removed a medication at the wrong time.

Each attendant workstation will communicate with a pharmacy workstation configured to help pharmacy workers fill the pillboxes. The pharmacy workstation will include blinking cabinet lights that indicate the location and quantity of each medication needed for an identified pillbox. Pillbox lights will show the pharmacy personnel where to put each medication in the identified pillbox, and filling errors will be automatically detected. Blinking cabinet lights will also show the pharmacy workers which storage boxes contain missing medications and which storage boxes might contain the wrong medications. When pharmaceutical companies start labeling medications with RFID tags, an RFID antenna under each compartment of the pillbox will automatically verify that each RFID tagged medication is in the correct compartment of the pillbox.

The attendant workstation computer will periodically communicate with the pharmacy computer to determine when a medication is late. A "late medication" alarm code will be first sent to a central monitoring station and if no acknowledgement occurs within a specified time period, the alarm code will be automatically transmitted to the appropriate attendant's wireless communication device.

Each attendant workstation will also monitor a collection of RF antennas in the patient's room, which will detect a variety of other dangerous situations. One or more RF antennas inside or under the patient's mattress will be used to automatically read RFID tags on the patient's wrists and/or ankles. The ankle tags can be attached to non-skid socks at any location close to the top of each foot. The workstation computer will periodically identify the patient while lying on the mattress to detect medication errors. The workstation computer will also monitor antennas under floor coverings and under the shower tub to identify close proximity of either wrist tag, which will be interpreted as a possible fall. Bed egress will be detected when the mattress antenna(s) are unable to identify any wrist or ankle tag or when the floor antennas identify close proximity of either ankle or sock tag. Wandering will be detected via antenna(s) inside the door, door frame or floor covering close to the door, i.e. when these antenna(s) identify the proximity of any tag.

Alternatively, the patient can wear small battery powered ID tags that periodically transmit an RF signal that identifies the patient and whether each tag is located on the patient's wrist or ankle. In this situation, the RF antennas inside the mattress, under the floor coverings, under the shower tub, inside the door or door frame, and at other locations do not transmit an RFID signal. Instead, they only receive the RF signals transmitted by the active RF tags. The power of each transmitted RF signal can be limited to achieve the desired detection range. For example, a detection range of 12 inches will be appropriate for ankle tags, and a detection range of 24 inches will be appropriate for wrist tags. Frequency hopping or other schemes will allow each RF antenna to read multiple active tags at the same time.

When a patient is identified via a mattress, floor or doorway antenna, the workstation computer will automatically access the patient's records to determine if any wandering or bed restraints have been noted and to also determine the patient's preferred language. When an alarm situation has been identified, the workstation computer will send an appropriate alarm code to the central monitoring station and/or to the responsible attendant's wireless communication device. The workstation computer can also play prerecorded voice commands in the patient's preferred language, such as "Michael, please stay in your room."

Other features and advantages of the present invention will be readily appreciated upon review of the following detailed description when taken in conjunction with the accompanying drawing figures.

DETAILED DESCRIPTION OF THE EMBODIMENTS

Figure 1:
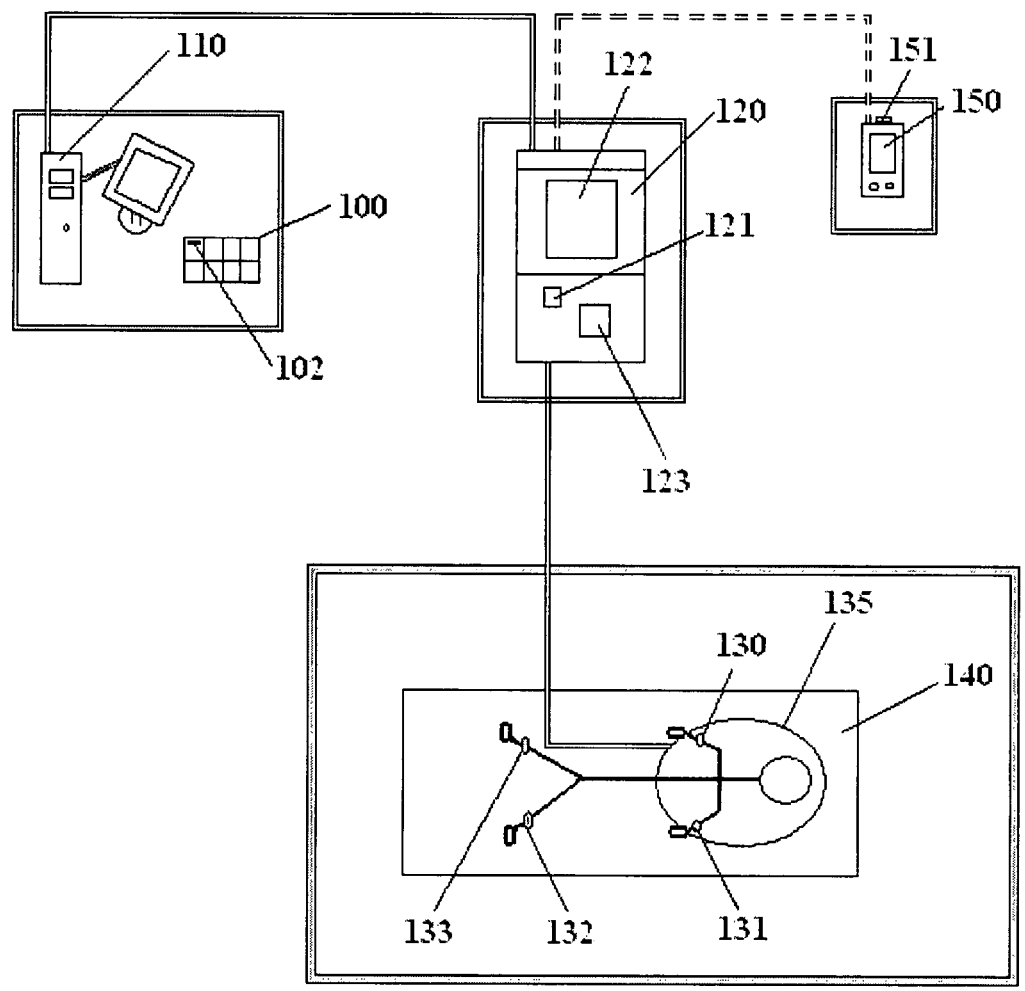
FIG. 1 is a diagram illustrating interconnections between an attendant workstation, a pharmacy workstation, an RF antenna located inside or under the patient's mattress, and an attendant's wireless communication device.

FIG. 1 is a block diagram illustrating communications between an attendant workstation 120, a pharmacy computer 110, an RF antenna and transceiver circuit 135 inside or under the patient's mattress, and an attendant's wireless communication device 150. Most institutions will also want hardwired communications with a nurses' station or other central monitoring station computer, which is not shown. A computer associated with the workstation 120 also communicates with RFID devices inside the patient's room that detect medication errors, falls, bed egress and room egress (i.e. wandering).

Figure 2:
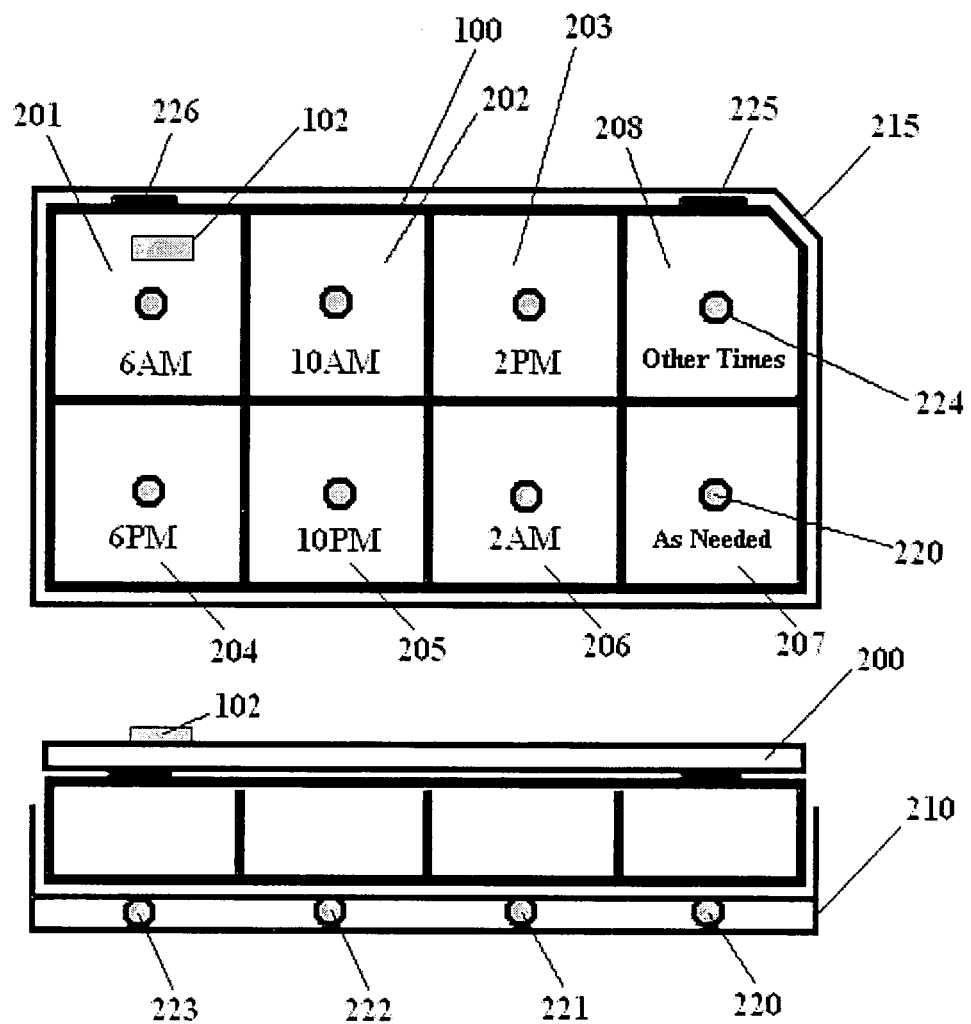
FIG. 2 is a conceptual illustration of an RFID pillbox with separate compartments for medications, and a light under each compartment shows pharmacy workers where to insert each prescribed medication.

FIG. 2 illustrates an RFID pillbox 100 with separate compartments 201-208 for pills, and pillbox lights 220 under each compartment that show pharmacy workers where to insert each prescribed medication.

Figure 3:
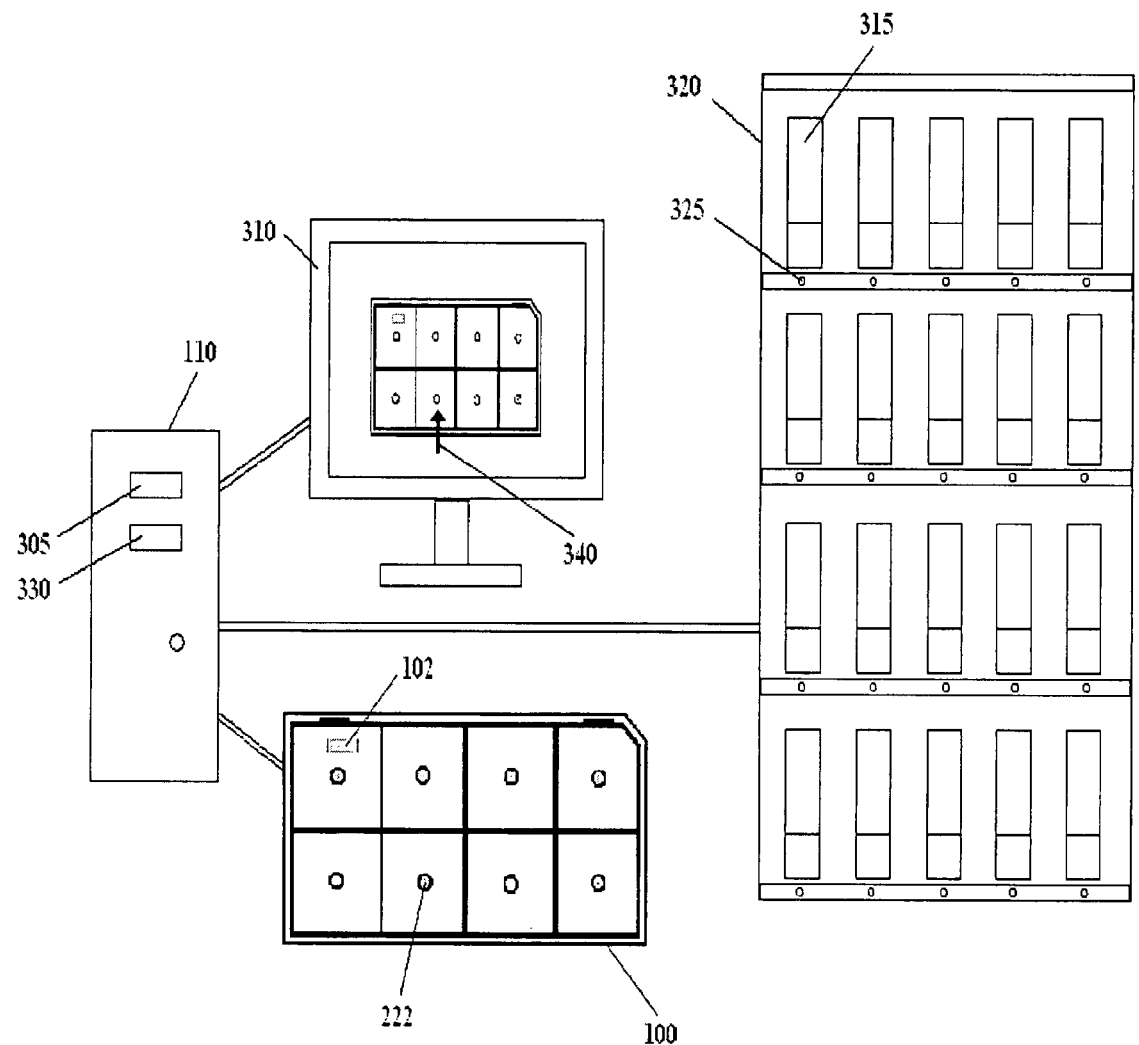
FIG. 3 is a diagram illustrating the filling of RFID pillboxes at a pharmacy workstation.

FIG. 3 illustrates the pharmacy computer 110 helping pharmacy workers find a storage box 315, where a prescribed medication is stored. A blinking cabinet light 325 indicates the quantity and location of the medication.

Figure 4A:
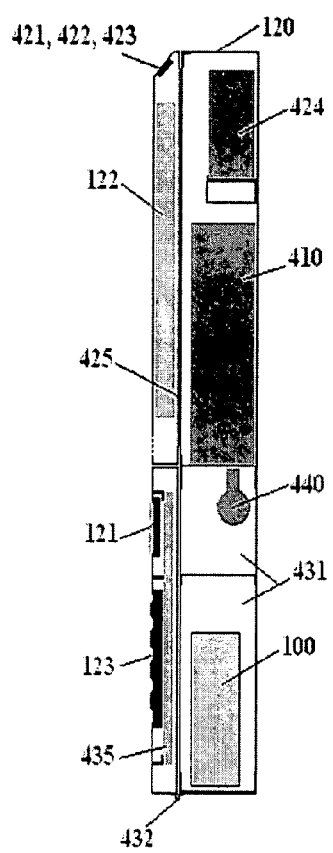
FIG. 4a is a side view of a wall-mounted attendant workstation cabinet containing a workstation computer, an RFID pillbox, and other electronics.
Figure 4B:
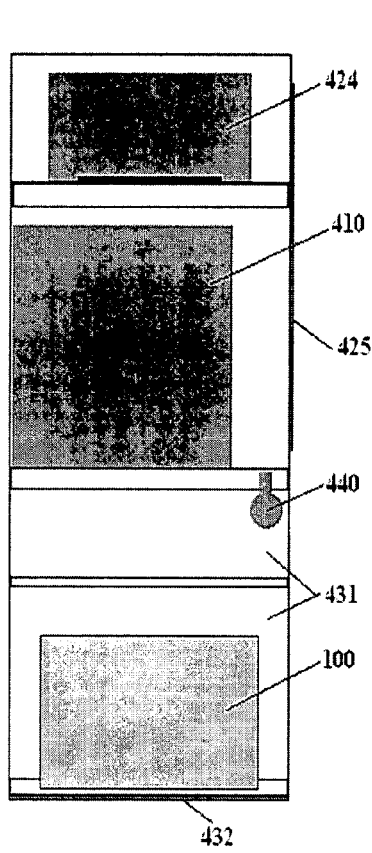
FIG. 4b is a front view of the attendant workstation cabinet with the front doors removed.
Figure 4C:
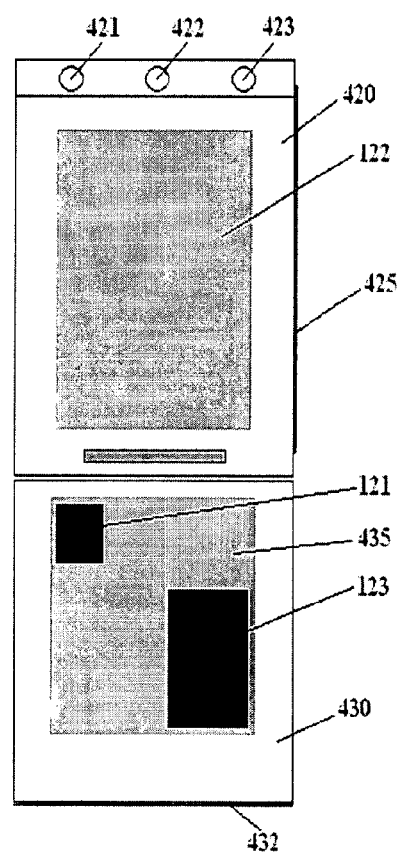
FIG. 4c is a front view of the top and bottom doors of the attendant workstation cabinet.

FIG. 4a is a side view of a wall-mounted attendant workstation cabinet 120 containing a workstation computer 410, a pillbox 100 and other electronics. FIG. 4b is a front view of the workstation cabinet 120 with the front doors removed, and FIG. 4c is a front view of the top door 420 and bottom door 430 of the workstation.

Figure 5:
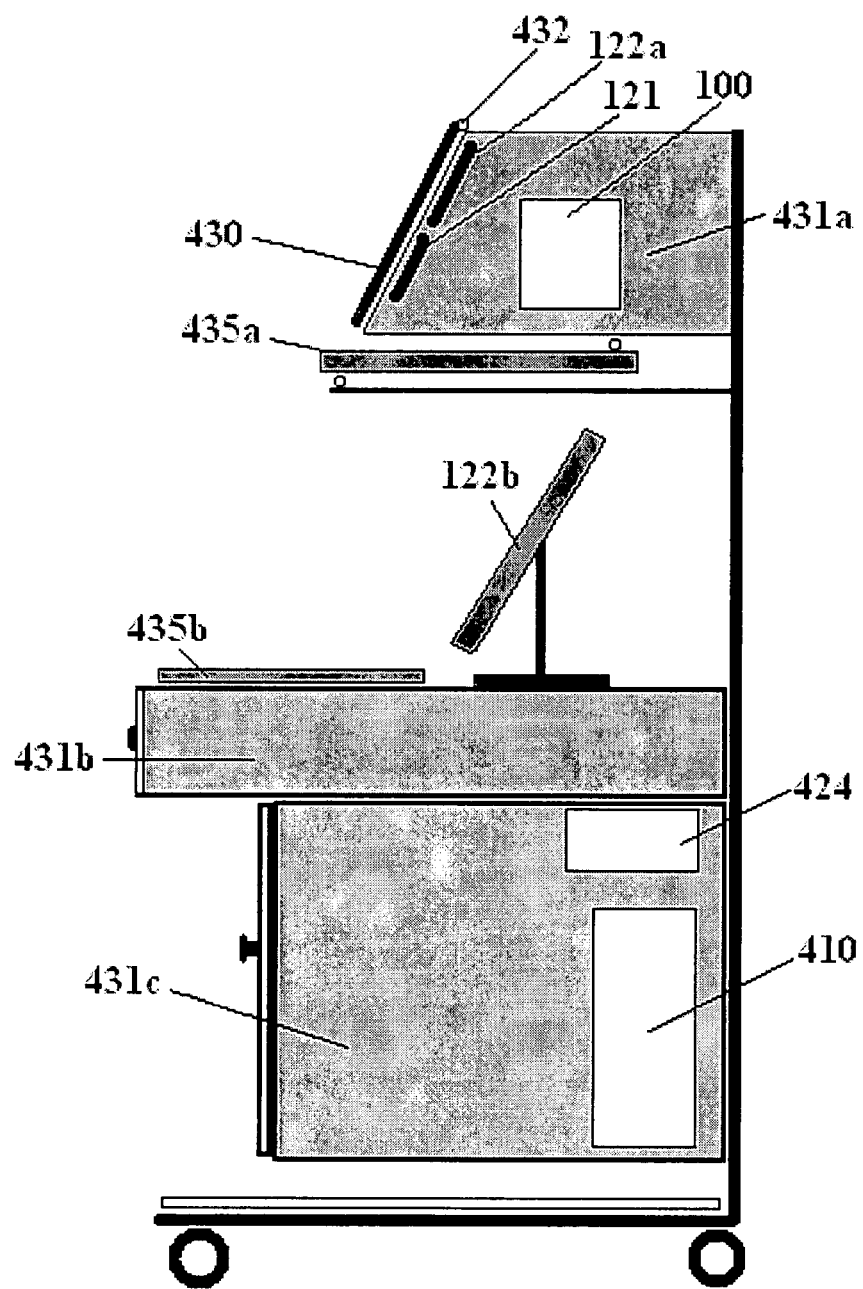
FIG. 5 is a conceptual illustration of an attendant workstation cabinet configured as a computer desk with a separate computer monitor and keyboard for patients and their guests and an RFID pillbox located inside a locked compartment above the computer monitor.

FIG. 5 shows the workstation cabinet 120 configured as a computer nightstand with a separate computer monitor 122b and keyboard 435b for patients and their guests. The pillbox 100 is stored inside a locked compartment above the patient's computer monitor 122b.

Figure 6:
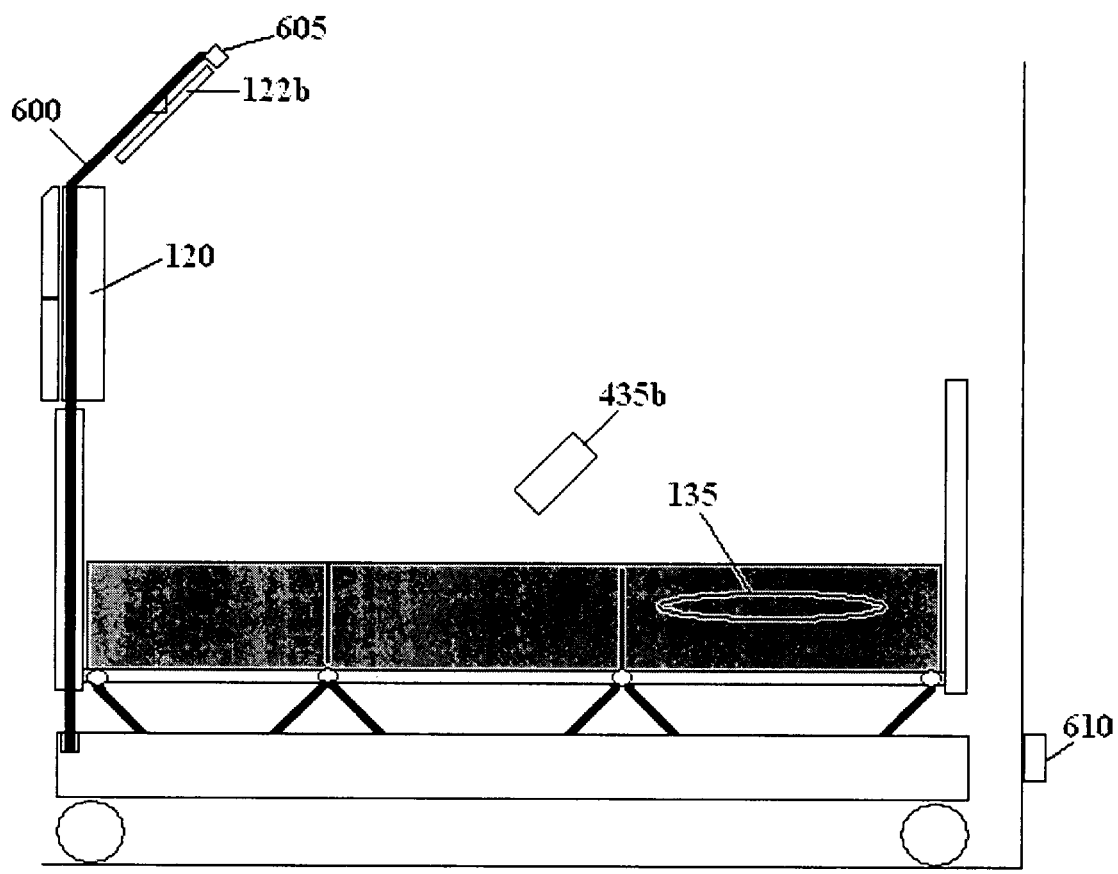
FIG. 6 is a conceptual illustration of an attendant workstation cabinet that plugs into sockets at the foot-end of a hospital bed, and this workstation includes a camera, microphone and speaker for video communications with the patient.

FIG. 6 shows a workstation cabinet 120 attached to a frame 600 that plugs into sockets at the foot-end of a hospital bed. A second computer monitor 122b and wireless keyboard 435b can be used by the patient. A camera, microphone and speaker 605 are also shown attached to the frame 600 for video communications with the patient.

FIG. 1 illustrates how a pillbox 100 is filled in a hospital pharmacy department using a pharmacy computer 110 programmed to oversee the process. FIG. 3 shows how a blinking cabinet light 325 identifies the location and quantity of a prescribed medication. FIG. 2 depicts pillbox lights 220 positioned under the pillbox 100, which helps the pharmacy technician insert each identified medication into the correct compartment of the pillbox 100.

In this system, each patient is assigned unique RFID codes for a pillbox tag 102, wrist tags 130 and 131 and optional ankle tags 132 and 133. In an embodiment well suited for use in hospitals, the workstation cabinet 120 is mounted to wall studs just outside the patient's room. An RFID reader 121 inside the workstation cabinet 120 reads the pillbox Tag 102, and an RFID reader 135 inside the patient's mattress periodically reads the patient's wrist tag 130 or 131. The attendant workstation 120 communicates with both RFID readers 121 and 135 and identifies when the pillbox 100 has been delivered to the wrong patient. Details about any identified errors are displayed on the workstation monitor 122.

The patient's pillbox 100 is stored in a locked compartment inside the attendant workstation cabinet 120. The pillbox compartment is unlocked when an attendant's RFID badge is detected by the RFID reader 121 followed by the attendant entering a pre-approved personal identification number ("PIN") and/or password. The PIN and/or password inputs are registered using a Keypad 123 attached to the workstation 120.

Each day or night, a second pillbox 101 with the same RFID tag 102 is filled with medications prescribed for the next day. At a specified time, pillbox 101 is delivered to the patient's workstation cabinet 120 and exchanged for pillbox 100. The following day or night, pillbox 100 is refilled and exchanged for pillbox 101.

The attendant workstation 120 computer communicates with the pharmacy computer 110 to determine all of the medications prescribed for the patient and a deadline for each medication. When a medication is late, a "late medication" message or alarm code is displayed on the attendant workstation monitor 122 and/or central workstation monitor. The message can be also transmitted to a wireless communication device 150 carried by the responsible attendant. The wireless communication device 150 can be also configured with a barcode reader 151 for reading barcode labels on patient's ID bracelets and for reading barcode labels on medication wrappers.

In a preferred embodiment of the invention, the "late medication" message or code is first displayed on the central workstation monitor listing the patient's name, room number, and other details. The attendant at the central workstation must press a special function key within a specified period of time to acknowledge the message. If no response is detected by the central workstation computer, then a similar wireless message is automatically transmitted by the central workstation computer to the responsible attendant's wireless communication device 150. The central workstation monitor can be located at the responsible nurses' station.

The wireless communication device 150 can be also used for other text, audio and video communications, e.g. displaying other alarm codes, displaying distorted video images of floor areas where patient falls have been detected and seeing a clear video image of the patient during nurse call communications. These video options must be pre-approved by the patient during the admissions process. The wireless communication device 150 can be a PDA, a cell phone, or a small laptop computer.

If pharmaceutical companies switch from barcode labels to RFID tags on medication wrappers, the same RFID reader 121 inside the attendant workstation cabinet 120 can be used to read all of the RFID medication tags inside the pillbox 100 and can thereby detect when a medication has been removed from the pillbox 100 at the wrong time. The RFID reader 121 can also identify when any medications are missing at the time the pillbox 100 arrives at the attendant workstation 120 or when an arriving medication or dosage is incorrect. The attendant workstation computer can be programmed to display these error messages on the workstation monitor 122 and to also report these delivery errors to the pharmacy computer 110. In some applications, the RFID tag 102 on the pillbox 100 may be designed to operate at a different frequency than the RFID tags on wrapped medications. In this situation, a different RFID reader inside the workstation 120 will read the medication tags.

Most hospital patients will be expected to wear both RFID wrist tags 130 and 131, which will improve the accuracy for detecting medication errors, falls, bed egress and room egress. Patients with a history of wandering will also wear ankle tags 132 and 133 attached to ankle bracelets or socks. RF antennas under hallway flooring coverings will identify ankle tags 132 and 133 and will detect when a patient with a history of wandering has entered an unsafe area.

The computer associated with the attendant workstation 120 will monitors the interfacing circuits connecting to RF antennas under floor coverings inside the patient room and under the shower tub to detect when either wrist tag 130 or 131 remains close to the floor at these locations, which will be interpreted as a patient fall. Bed egress will be indicated when neither wrist tag 130 nor 131 is detected by an RF antenna 135 inside or under the mattress. Room egress will be detected when an RF antenna inside the entry door or door frame detects close proximity of either wrist tag 130 or 131. Bed egress can be also indicated when either ankle tag 132 or 133 is detected by a floor antenna next to the bed, and room egress can be identified when either ankle tag 132 or 133 is detected by a door antenna, door frame antenna or floor antenna next to the door.

FIG. 2 shows more details about pillbox 100. A passive RFID tag 102 is attached to the pillbox 100. When the RFID tag 102 is triggered to transmit, it conveys an alphanumeric code which is assigned to the patient during the admissions process. The pillbox 100 has separate compartments 201, 202, 203, 204, 205, 206 . . . for holding medications which are scheduled for delivery to the patient at marked standard times, e.g. 6 AM, 10 AM, 2 PM, 6 PM, 10 PM, 2 AM, etc. Additional compartments 207, 208 are for medications prescribed as needed or at non-standard times. Each patient is assigned two identical pillboxes 100 and 101 (pillbox 101 is not shown). An identical RFID tag 102 number is attached to both pillboxes 100 and 101, thereby identifying that the pillboxes 100 and 101 are both assigned to the same known patient.

FIG. 3 shows how the pharmacy computer 110 helps a pharmacy technician refill pillbox 100 and other pillboxes assigned to other patients. The patient's name, allergies, preferred language, room number and other information are determined via the RFID tag 102 and associated patient records. The pharmacy technician uses an RFID reader 305 to read the RFID tag 102. The pharmacy computer 110 then looks up the patient's prescriptions, and the computer monitor 310 displays a drawing of the pillbox 100 and other details about the patient.

The pillbox 100 is then inserted into a refill tray 210 with a different edge 215 at one corner which matches one corner of the pillbox 100, thereby forcing the pillbox 100 into a preferred orientation inside the refill tray 210. Alternatively, hinges 225 and 226 can be used that only fit into the refill tray 210 when properly aligned. Many other alignment schemes can be employed. A collection of pillbox lights 220, 221, 222, 223, 224 . . . are mounted at the bottom of the refill tray 210 with each pillbox light able to project light through the bottom surface of one of the compartments of the pillbox 100.

All of the stock medications are stored in a collection of storage boxes 315 positioned on shelves of an Instrumented cabinet 320. When the pharmacy computer 110 determines all of the medications prescribed for the patient, the pharmacy computer 110 turns on a cabinet light 325 under each of the storage boxes 315 containing medications which have been prescribed for the patient. Each cabinet light 325 blinks a number of times that indicates the number of pills which need to be inserted into the pillbox 100 for the identified patient. After blinking, each cabinet light 325 remains off for a short period of time, and then automatically repeats the sequence of blinks. The pharmacy technician must walk along each shelf and collect the correct number of pills from each storage box 315, as indicated by the blinking light below each storage box 315. In an alternative design, the cabinet lights 325 can be mounted above the storage boxes 315. Also, a small 2-digit display can be mounted under or over each storage box 315 to show the number of pills needed. Other liquid medications and supplies can be selected via the same scheme.

The pharmacy worker must next use a barcode reader 330 to read the barcode label on each wrapped medication. The barcode reader 330 can be built into the pharmacy computer 110 or it can be a handheld barcode reader (not shown). The pharmacy computer 110 then looks up the patient's prescription records and displays an Arrow 340 or other indicator on the pharmacy monitor 310, showing the pharmacy technician where to put the medication in the pillbox 100. To assist the technician, a pillbox light 222 under the pillbox 100 turns on to further indicate where the medication should be placed in the pillbox 100. The pillbox light 222 remains on until the next medication barcode label is read. A sound is triggered each time a medication label is successfully read. A different sound is triggered each time a medication label is detected but not identified.

When all of the barcode labels have been read, any missing medications are listed on the computer monitor 310, and the corresponding cabinet lights 325 on the Instrumented cabinet 320 blink to show the pharmacy technician the location and quantity of the remaining medications needed. The pharmacy worker must again use the barcode reader 330 to read each of the remaining medication labels. The pharmacy monitor 310 and appropriate pillbox light show the pharmacy worker where to place each of the missing medications. If any medications are wrong, the pharmacy computer 110 will help the pharmacy worker identify the storage boxes 315 which may contain the wrong medications. The pharmacy monitor 310 will display a warning message instructing the pharmacy technician to check each of the suspected storage boxes 315 marked by a rapidly blinking cabinet light 325. The cabinet lights 325 will blink rapidly one at a time, and the pharmacy monitor 310 will list the medication that should be in the identified storage box.

If pharmaceutical companies shift from barcode labels to RFID tags on wrapped medications, the RFID reader 305 can be used to read each medication tag. Alternatively, a separate RFID antenna could be mounted around each of the pillbox lights 220 to read all of the medication tags inside each pillbox compartment 201. The pillbox 100 could be fabricated with a clear plastic bottom, a metal lid, and metal sides around each compartment 201. This design would shield the tags in adjacent compartments.

Each pillbox 100 is stored inside a locked attendant workstation cabinet 120, exemplified as a wall-mounted cabinet in FIGS. 4a, 4b, and 4c. This cabinet design is recommended for hospitals. The wall-mounted cabinet 120 is designed to fit between wall studs and protrude out of the wall as little as possible. FIG. 4a shows a side view of the cabinet and contents; FIG. 4b shows a front view with both the top and bottom doors removed; and FIG. 4c shows the top and bottom doors with several electronic devices attached to each door. On the first day, the pillbox 100 is filled and delivered by the pharmacy department with medications prescribed for the first day. The pillbox 101 is filled and exchanged for the pillbox 100 before the morning of the second day.

The hospital version of the attendant workstation cabinet 120 can be located inside or just outside the patient's room. A wall-mounted cabinet just outside the patient's room will have significant advantages of (1) giving the nurses more privacy when reading or typing patient records and preparing each medication delivery; (2) making it easier for pharmacy technicians to deliver the pillboxes without losing site of their delivery cart; (3) keeping the medications and supplies away from infectious organisms inside the patient's room; and (4) displaying alarm codes and email messages on the workstation monitor at a more visible location that will be less likely to frighten the patient.

In FIG. 4, the RFID reader 121 is used to read the RFID tag 102 attached to each pillbox 100, 101 and to also read each attendant's RFID badge. The attendant can access the locked workstation 120 by swiping his/her RFID badge close to the RFID reader 121 and by next inputting a pre-approved PIN and/or Password using the Keypad 123. A biometric reader (e.g. fingerprint reader, palm reader, or face recognition camera) can be provided with the attendant workstation 120 to add another level of security. Most biometric readers are expensive; therefore, this option is not shown in FIG. 4. Three levels of security can be created by requiring each attendant to first swipe an RFID badge near the RFID reader 121 and to next input a long-term PIN followed by a second short-term PIN. The short-term PIN could be changed each week or month at any workstation 120.

As previously described in the context of FIG. 1, RFID tags 130, 131, 132 and 133 remain close to each patient's body, for example on wristbands and attached to nonskid socks or ankle bracelets. Some institutions may not require all patients to wear ankle tags 132 and 133, but these RFID tags can be hidden inside non-skid socks and will prevent wandering and falls at minimal cost to the institution. RF antennas under floor coverings or floor mats in hallways, bathrooms and next to the bed identify when the patient is standing or walking at these locations. The workstation computer 410 can be programmed to first identify the patient and then access patient records to determine whether any wandering limits or bed egress restrictions have been imposed for the patient. The workstation computer 410 can then respond accordingly via alarm codes or prerecorded voice commands to the patient in the patient's preferred language.

An RFID antenna and transceiver 135 inside or below the patient's mattress are used to periodically read the patient's wrist tags 130 or 131. The workstation computer 410 periodically communicates with the RFID transceiver 135 (shown in FIG. 1) to identify the patient while lying in the bed. When a pillbox RFID tag 102 (shown in FIG. 1) is identified by the workstation RFID reader 121, the workstation computer 410 verifies that the patient is receiving the correct pillbox 100. Any errors are displayed on the attendant workstation monitor 122 mounted to the upper door 420 of the workstation cabinet 120.

Fans 421, 422, and 423 are mounted to the upper door 420 to cool the computer 410 and workstation monitor 122. A back-up batter power supply 424 is mounted above or below the workstation computer 410 for short periods of power loss.

Hospital generators will supply power to the workstation 120 during prolonged periods of power loss. The upper door 420 has a vertical hinge 425, allowing the upper door 420 to swing outward to access the computer 410 and other electronics.

An attendant can unlock the lower door 430 to access the storage compartment 431 by first swiping a pre-authorized RFID badge close to the RFID reader 121 and by next inputting a pre-approved PIN and/or Password using the Keypad 123. The hinge 432 for the lower door 430 is horizontal, allowing this door 430 to swing downward and remain in a horizontal position. A keyboard 435 is then positioned at a comfortable location for accessing patient records and typing email messages or patient records.

Each wrapped medication inside the pillbox 100 is marked with a distinctive barcode label. A barcode reader 440 mounted inside the storage compartment 431 is used to read the barcode label on each medication before the medication is delivered to the patient. The attendant workstation computer 410 communicates with the pharmacy computer 110 and with the mattress RFID transceiver 135 to identify any medication errors, e.g. incorrect medications, incorrect dosages, missing medications, or timing errors. Error messages are displayed on the workstation monitor 122 and reported to the pharmacy computer 110.

When the patient is out of the bed, a wireless barcode reader near the patient's bed can be used to read either barcode label printed on both of the patient's ID bracelets, i.e. next to the RFID tags 130 and 131. Some institutions may prefer to provide each attendant with a wireless communication device 150 configured with a barcode reader 151.

The workstation computer 410 communicates with the pharmacy computer 110 at periodic intervals to determine prescribed medications and deadlines for medication deliveries for the identified wrist tag 130 or 131. Whenever a critical medication has not been identified by the barcode reader 440 or 151 before the prescribed deadline indicated by the pharmacy computer 110, a "late medication" message is sent to a central monitoring station, and the message can be optionally forwarded to the responsible attendants wireless communication device 150. If the workstation computer 410 does not identify that the late medication has been delivered in a specified period of time, the "late medication" alarm code is sent again and repeated at specified intervals until the medication is identified.

Some institutions may want their attendants to carry a wireless PDA 150, which can be easily configured with a barcode reader 151. The attendant can use the wireless PDA 150 and attached barcode reader 151 to read barcode labels in the patient's room, to receive and transmit text or audio messages, and to also see a video image of a patient. If an institution is not able or willing to provide wireless PDA's 150 for their attendants, alarm codes can be transmitted to responsible attendants using less expensive telephone pagers. For example, a telephone pager message of "042-0891" could signify that a Code "042" (decoded as a late medication) has been detected by the workstation computer 410 at room "0891." Other number codes could be used to indicate patient falls, wet sheets, bed egress, room egress, and when weight-shifts are needed.

In hospitals and nursing homes with more than one bed per room, a larger compartment inside the workstation cabinet 120 can be provided for multiple pillboxes. When a pillbox is identified and the patients inside the room are identified via an RFID antenna and transceiver inside or below each mattress 135, the workstation monitor 122 displays a drawing of the room, an optional photograph of the patient and indicates which bed the patient is residing. In this situation, a second barcode check inside the patient room is particularly important, i.e. reading the barcode label on the patient's ID bracelet and the barcode label on each medication.

The attendant workstation cabinet 120 can be attached to a wall as described above or contained inside a computer desk as depicted in FIG. 5. This design will be less appealing to most hospitals for the reasons described above, but may be more appealing to assistive living centers and nursing homes. FIG. 5 shows a workstation computer 410 and back-up battery supply 424, two keyboards 435a and 435b, two workstation monitors 122a and 122b, one RFID reader 121, three storage compartments 431a, 431b, and 431c, a locked cabinet door 430 with a horizontal hinge 432, and pillbox 100. The lowest storage compartment 431c can also contain an optional refrigerator for intravenous bags. The workstation computer 410 can be set up to allow patients to use the desktop keyboard 435b, computer monitor 122b and middle storage Drawer 431b. The other two storage compartments 431a and 431c can be locked, requiring a pre-approved RFID badge and PIN to access these compartments. The upper keyboard 435a slides outward toward the attendant for inputting the attendant's PIN and accessing patient records. The upper cabinet door 430a has two square holes (not shown) for accessing the RFID reader 121 and for viewing the upper computer monitor 122 when the cabinet door 430a is in a locked position. The cabinet door 430a rotates upward to access the pillbox 100 and upper storage compartment 431a.

FIG. 6 shows another configuration of the attendant workstation cabinet 120 mounted to the foot-end of a hospital bed, e.g. plugging the workstation frame 600 into the sockets provided on most hospital beds for an over-bed trapeze frame. A second computer monitor 122b is mounted to the workstation frame 600 to allow the patient to see the monitor 122b while lying in the bed, and a wireless keyboard and mouse pad 435b is available to the patient and guests for a variety of computer applications including Internet access.

A digital camera, microphone and audio speaker 605 can be attached to the frame 600 or enclosed with the computer monitor 122b for audio and video communications with attendants, physicians and family members. A multi-lead electrical connector 610 will need to be installed near the headwall with appropriate electrical connections for the workstation computer 410 and other electronics provided with the workstation 120. A mobile version of the bed frame workstation 120 could be offered with the workstation frame 600 attached to a stand that rolls under the foot-end of the bed.

The workstation computer 410 in each of the above configurations monitors RF antennas at different locations in the patient's room, for example (1) the RF antenna(s) 135 inside the mattress for reading either wrist tag 130 or 131 at periodic intervals to detect medication errors; (2) the same RF antenna(s) 135 inside the mattress for identifying when neither wrist tag 130 nor 131 are close to the mattress which will be interpreted as bed egress; (3) the RF antenna(s) under floor coverings or floor mats for identifying prolonged proximity of either wrist tag 130 or 131 which will be interpreted as a patient fall; (4) the RF antenna(s) under a shower tub for identifying prolonged proximity of either wrist tag 130 or 131 which will be interpreted as a patient fall in the shower tub; (5) the RF antenna(s) inside the entry door or door frame for identifying close proximity of either wrist tag 130 or 131 which will be interpreted as room egress; and (6) the RF antenna(s) under floor coverings or floor mats in hallways, at doorways next to the bed, next to the toilet and at other locations for identifying close proximity of either ankle tag 132 or 133. These RF antennas and tags will be used to detect wandering outside the patient's room and will also detect when a patient gets out of the bed and when the patient has entered the bathroom. If the patient is wearing RFID tags, the antennas transmit and receive RFID signals via transceiver circuits. If the patient is wearing battery powered RF tags that automatically transmit an RF signal at periodic intervals, then the antennas are only used to receive the RF signals, and receiver circuits amplify the signals. It should be understood that the foregoing relates only to the exemplary embodiments of the present invention, and that numerous changes may be made therein without departing from the spirit and scope of the invention as defined by the following claims.

The invention claimed is:

1. A method for identifying a person on a mattress on a bed and generating an alert comprising:
    detecting an RF identification signal transmitted by at least one identification device on the person, wherein the at least one identification device is activated by an RF signal transmitted by an antenna associated with at least one of the mattress and bed frame;
    generating an alert when at least one identification device associated with a lower limb of the person is activated by an antenna associated with the floor, if the data associated with the person derived from any identification device associated with the person indicates that the person is not allowed to get out of bed without assistance;
    accessing data associated with a second person in the room occupied by the person by decoding a wireless signal transmitted by an identification device on the second person, wherein the wireless identification device on the second person is activated by at least one of the antenna associated with the mattress, an antenna associated with the floor, and an antenna associated with a door; and
    cancelling the alert if the second person is identified as being an attendant.

2. The method of claim 1, wherein the antenna associated with the floor comprises an antenna associated with a floor covering.

3. The method of claim 1, wherein the antenna associated with the floor comprises an antenna associated with a floor mat.

4. The method of claim 1, wherein the antenna associated with the floor comprises an antenna associated with a shower tub floor.

5. The method of claim 1, wherein if the person is not allowed to get out of bed with assistance and if there are no second persons in the room, accessing the data associated with the person to determine the person's preferred language and generating an audible command in the person's preferred language instructing the person to stay in the bed.

6. The method of claim 1, wherein the method further comprises:
    using the antenna associated with at least one of the mattress and bed frame to monitor tagged medication deliveries to the person's room;
    accessing prescription records for the identified person in each bed; and
    generating an alert if an incorrect medication has arrived at the person's room or has arrived at the wrong time; and
    generating a late medication alert if a medication has not arrived before a specified time after the prescribed time of delivery.

7. A method for generating an alert if a person has fallen comprising:
    generating an alert when at least one identification device associated with a person's upper body is activated for a prolonged period of time by an antenna associated with the floor;
    accessing data associated with a second person in the room occupied by the person by decoding a wireless signal transmitted by an identification device on the second person, wherein the wireless identification device on the second person is activated by at least one of the antenna associated with a mattress, an antenna associated with the floor, and an antenna associated with a door; and
    cancelling the alert if the second person is identified as being an attendant.

8. The method of claim 7, wherein the antenna associated with the floor comprises an antenna associated with a floor covering.

9. The method of claim 7, wherein the antenna associated with the floor comprises an antenna associated with a floor mat.

10. The method of claim 7, wherein the antenna associated with the floor comprises an antenna associated with a shower tub floor.

11. The method of claim 7, further comprising:
    using the antenna associated with the floor of the person's room to monitor tagged medication deliveries to the person's room;
    accessing prescription records for the identified person in each bed; and
    generating an alert if an incorrect medication has arrived at the person's room or has arrived at the wrong time; and
    generating a late medication alert if a medication has not arrived before a specified time after the prescribed time of delivery.

12. A method for generating an alert when a person enters a bathroom comprising:
    if any identification device associated with the person is activated by an antenna associated with the bathroom, accessing the identified person's records and determining whether bathroom entry is permitted;
    generating an alert if bathroom entry is not permitted;
    accessing data associated with a second person in the room occupied by the person by decoding a wireless signal transmitted by an identification device on the second person, wherein the wireless identification device on the second person is activated by at least one of the antenna associated with the mattress, an antenna associated with the floor, and an antenna associated with a door; and
    cancelling the alert if the second person is identified as being an attendant.

13. The method of claim 12, wherein the antenna associated with the bathroom is an antenna associated with the bathroom door.

14. The method of claim 12, wherein the antenna associated with the bathroom is an antenna associated with the bathroom doorframe.

15. The method of claim 12, wherein the antenna associated with the bathroom is an antenna associated with the bathroom floor covering.

16. The method of claim 12, wherein if the patient continues to enter the bathroom when a second person is not identified in the room, accessing the patient's records to determine the patient's preferred language and generating an audible command in the patient's preferred language instructing the patient to call for assistance before entering the bathroom.

17. A method generating an alert if a person is exiting comprising:
    if any identification device associated with the person is activated by an antenna associated with an exit, accessing the identified person's records and determining whether room exit is permitted;
    generating an alert if room exit is not permitted;

accessing data associated with a second person in the room occupied by the person by decoding a wireless signal transmitted by an identification device on the second person, wherein the wireless identification device on the second person is activated by at least one of the antenna associated with the mattress, an antenna associated with the floor, and an antenna associated with a door; and cancelling the alert if the second person is identified as being an attendant.

18. The method of claim 17, wherein the antenna associated with the exit comprises an antenna associated with a door.

19. The method of claim 17, wherein the antenna associated with the exit comprises an antenna associated with a door frame.

20. The method of claim 17, wherein the antenna associated with the exit comprises an antenna associated with a floor covering near an exit doorway.

21. The method of claim 17, wherein if the patient continues to pass through the exit door when a second person is not identified in the room, accessing the patient's records to determine the patient's preferred language and generating an audible command in the patient's preferred language instructing the patient to stay in the room.

22. The method of claim 17, further comprising:
using the antenna associated with the exit to monitor tagged medication deliveries to the person's room;
accessing prescription records for the identified person in each bed; and
generating an alert if an incorrect medication has arrived at the person's room or has arrived at the wrong time; and
generating a late medication alert if a medication has not arrived before a specified time after the prescribed time of delivery.

* * * * *